(12) United States Patent
Le Noane

(10) Patent No.: US 11,896,469 B2
(45) Date of Patent: Feb. 13, 2024

(54) DISPENSER OF MENSTRUAL PRODUCTS AND CORRESPONDING REFILLS

(71) Applicant: Marguerite & Cie, Plobannalec-Lesconil (FR)

(72) Inventor: Gaële Le Noane, Plobannalec-Lesconil (FR)

(73) Assignee: MARGUERITE & CIE, Plobannalec-Lesconil (FR)

( * ) Notice: Subject to any disclaimer, the term of this patent is extended or adjusted under 35 U.S.C. 154(b) by 27 days.

(21) Appl. No.: 17/626,993

(22) PCT Filed: Jul. 2, 2020

(86) PCT No.: PCT/EP2020/068740
§ 371 (c)(1),
(2) Date: Jan. 13, 2022

(87) PCT Pub. No.: WO2021/008891
PCT Pub. Date: Jan. 21, 2021

(65) Prior Publication Data
US 2022/0273505 A1  Sep. 1, 2022

(30) Foreign Application Priority Data

Jul. 16, 2019  (FR) ..................................... 1908024
Aug. 13, 2019  (FR) ..................................... 1909191

(51) Int. Cl.
*A47F 1/08*  (2006.01)
*A61F 15/00*  (2006.01)

(52) U.S. Cl.
CPC .............. *A61F 15/003* (2013.01); *A47F 1/08* (2013.01)

(58) Field of Classification Search
CPC ...................................................... A47F 1/08
(Continued)

(56) References Cited

U.S. PATENT DOCUMENTS 3,450,308 A * 6/1969 Schoenefeld .......... B65D 5/724
                                                  229/906.1
3,860,304 A   1/1975 Bolton
(Continued)

FOREIGN PATENT DOCUMENTS

DE      29819738 U1    2/1999
DE      20308135 U1   10/2003
WO      2019074571 A1  4/2019

OTHER PUBLICATIONS

English translation of the Written Opinion of the International Searching Authority dated Oct. 2, 2020 for corresponding International Application No. PCT/EP2020/068740, filed Jul. 2, 2020.
(Continued)

*Primary Examiner* — Timothy R Waggoner
(74) *Attorney, Agent, or Firm* — David D. Brush; Westman, Champlin & Koehler, P.A.

(57) ABSTRACT

A menstrual product dispenser including a rear face, intended for attaching the dispenser to a vertical support, two side faces and a front face. The dispenser also includes: at least one storage compartment suitable for receiving at least one container comprising a plurality of the menstrual products, referred to as the product refill, each refill comprising a plurality of menstrual products of the same type, a base, which is rigidly connected to the rear face and the side faces, for retaining the at least one product refill in the dispenser, and at least one compartment for distributing at least one of the menstrual products. The at least one distribution compartment is rigidly connected to the base of the dispenser. The dispenser is suitable for distributing one menstrual product of each type in the distribution compartment.

8 Claims, 7 Drawing Sheets

(58) Field of Classification Search
USPC .................. 221/33–63, 197, 309; 312/42
See application file for complete search history.

(56) References Cited

U.S. PATENT DOCUMENTS

| | | | | |
|---|---|---|---|---|
| 4,767,022 A | * | 8/1988 | Oldorf | .................... G07F 11/18 |
| | | | | 221/92 |
| 5,167,345 A | | 12/1992 | Bleeker | |
| D371,707 S | * | 7/1996 | Miles | .............................. D6/515 |
| 5,642,837 A | * | 7/1997 | Hayes | .................... B65D 83/08 |
| | | | | 312/42 |
| 5,700,075 A | * | 12/1997 | Perone | ...................... A47F 1/08 |
| | | | | 312/45 |
| 5,836,661 A | * | 11/1998 | Oldorf | ...................... A47F 1/08 |
| | | | | 229/243 |
| 5,947,302 A | | 9/1999 | Miller | |
| 5,957,325 A | * | 9/1999 | Montanez | ................. A47F 1/08 |
| | | | | 221/281 |
| 6,415,949 B1 | * | 7/2002 | Tramontina | ......... A47K 10/424 |
| | | | | 221/45 |
| 7,147,129 B1 | * | 12/2006 | Menefield | ............... A61F 6/005 |
| | | | | 206/440 |
| 2005/0115979 A1 | | 6/2005 | Hellstrom et al. | |
| 2011/0114660 A1 | | 5/2011 | Johansson | |
| 2020/0317391 A1 | * | 10/2020 | Schultz | .................. B65D 5/725 |

OTHER PUBLICATIONS

International Search Report dated Sep. 22, 2020 for corresponding International Application No. PCT/EP2020/068740, dated Jul. 2, 2020.

Written Opinion of the International Searching Authority dated Sep. 22, 2020 for corresponding International Application No. PCT/EP2020/068740, filed Jul. 2, 2020.

European Notification under Article 94(3) EPC dated Nov. 25, 2022 for corresponding European Application No. 20 734 789.9.

* cited by examiner

DISPENSER OF MENSTRUAL PRODUCTS AND CORRESPONDING REFILLS

CROSS-REFERENCE TO RELATED APPLICATIONS

This Application is a Section 371 National Stage Application of International Application No. PCT/EP2020/068740, filed Jul. 2, 2020, which is incorporated by reference in its entirety and published as WO 2021/008891 A1 on Jan. 21, 2021, not in English.

TECHNICAL FIELD

The field of the present technique is that of distributing menstrual products, such as tampons or sanitary napkins. More particularly, the present technique relates to dispensers allowing free access to such menstrual products.

PRIOR ART

Some companies, some public bodies or some local, territorial or national communities (faculties, colleges, high schools, university residences, etc.) wish to offer free access, for example in the toilets of their premises, health products and in particular menstrual products, for reasons related to fighting inequalities and precariousness of women. Indeed, menstrual products could represent a very high cost for some women in great financial difficulty.

Dispenses of these products, in their marketed form (i.e. in the packaging intended to be sold) are already being implemented, for example in places intended for mutual aid and support, thanks to collections of products carried out before.

There is also a solution for distributing menstrual products in the form of dispensers having, for example, one or two product storage compartment(s), which then accumulate in an open compartment allowing free access to the products. However, this type of dispensers has at least two major drawbacks, namely the non-compliance with some hygiene rules essential for this product type and the lack of ergonomics and practicality for the people in charge of supplying these dispensers. Indeed, these dispensers should be filled, by their upper portion, with products "in bulk", which is not practical. In addition, the presence of a large number of products in the open compartment, and therefore possible access to several products when taking one for one's own use, pose obvious hygiene problems, not to mention handling of products "In bulk" at the time of supply to the dispenser.

Hence, there is a need for a solution for distributing menstrual products which is ergonomic for the users as well as for the people in charge of management thereof, while complying with the hygiene constraints related to this type of products.

DISCLOSURE OF THE INVENTION

The present invention addresses this need by providing a menstrual product dispenser comprising a rear face intended for attaching said dispenser to a vertical support, two side faces and a front face, and comprising:
- at least one storage compartment suitable for receiving at least one container comprising a plurality of said menstrual products, referred to as the product refill, each refill comprising a plurality of menstrual products of the same type,
- a base, secured to said rear face and said side faces, for holding said at least one product refill in said dispenser,
- at least one compartment for distributing at least one of said menstrual products, said at least one distribution compartment being secured to said base of said dispenser,
- and in that said dispenser is suited for distributing a single menstrual product per type in said distribution compartment.

Thus, the present technique provides a new and inventive solution for distributing menstrual products allowing not only for optimised management thanks to a dispenser designed so as to receive one or several refill(s) of these menstrual products but also for enhanced hygiene.

Thus, the dispenser of the present solution has one or several compartment(s) intended to receive one or several refill(s), for example each comprising one type of menstrual products (tampons, of different sizes, with or without an applicator, sanitary napkins of different sizes), thereby facilitating the supply of the dispenser but also the storage of the products. Indeed, the staff in charge of supplying a dispenser does not have to supply the dispenser directly with products, available for example "in bulk" in a bag or a box, but has just to insert one or several refill(s), solid and closed, in the dispenser, then open each refill to make the products available, as described hereinafter.

Moreover, such a dispenser allows providing several different types of products, thanks to several compartments each enabling the reception of a refill of different products.

In addition, this refill system allows complying with the hygiene constraints related to menstrual products, in terms of both the management of the dispensers and the time of use thereof.

Thus, the use of closed refills to supply the dispenser allows avoiding any direct handling of the products at the time the dispenser is supplied.

Similarly, these hygienic constraints are also met when distributing the menstrual products, thanks to the specific shape of the distribution compartment and to the opening provided in the storage compartment, which allow limiting the number of available products, by making only one product accessible at a time (or more exactly one product of each type at a time, if several types of products are dispensed). In this manner, a user only has access to the product that she is going to use, without touching one or several other product(s) intended for another user later on.

According to a particular feature, the front face has at least one lower opening opposite said at least one distribution compartment, said opening having a shape and dimensions suited for distributing a single menstrual product per type in said distribution compartment.

Thus, the front face has an opening adapted to enable the descent of the products of the refill towards the distribution compartment so that only one product of each type is accessible at a time, also thanks to the lower shape of the refills as described hereinafter.

In this manner, the hygiene constraints are met, as well as an optimised operation of the dispenser by avoiding any blockage or clogging of products in the refills.

For example, the opening formed in the front face has at least one gripping notch.

Thus, according to this embodiment, the lower opening is intended to facilitate gripping of a product in the distribution compartment, while preventing access to several products of the same type.

Indeed, to facilitate the taking of a product, a simple solution would have consisted in providing a wider lower opening. However, such a solution would have favoured the descent of several products (per type) into the distribution compartment, thereby contravening the hygiene requirements already mentioned hereinabove.

In addition, as will be described hereinafter, in connection with the product refills, this notch has a dual function and also enable opening of the refill once inserted into the storage compartment. Indeed, a similar pre-cut notch on the closed refill is located opposite the notch of the front face when the refill is inserted and a simple press on the refill, via the notch on the front face, allows cutting of the refill and opening of the lower portion to release the products towards the distribution compartment.

Preferably, the gripping notch is centred with respect to the width of the storage compartment.

In addition, the size of this notch, and more particularly its height, may be variable. According to a first variant, it has a height of about one centimetre allowing obtaining the desired technical effect. According to a second variant, it has a height of up to ten centimetres, so as to further enable a possible release of the products in the refill, while allowing visibility of the stock of products remaining in the refill.

According to a particular feature, the dispenser comprises at least two storage compartments separated by a vertical wall substantially parallel to said side faces, said at least two storage compartments each receiving a product refill.

Thus, when the dispenser comprises at least two storage compartments, it is possible to insert only a single refill that will not only be guided in the dispenser but also held in an appropriate position by the vertical wall, including in the absence a refill in the neighbouring compartment.

Indeed, without this wall, the isolated refill could not remain vertical in the dispenser and therefore prevent the products from descending towards the distribution compartment.

Such a wall corresponds for example to a simple guide rail, more or less deep, secured to the rear face, or to the front face of the dispenser. Such a wall may also correspond to a solid partition passing through the dispenser from the rear face to the front face.

According to a particular aspect of the dispenser, its base has an angle larger than 90° with said rear face.

Thus, the shape of the base of the dispenser, adapted to that of the base of the refills (as described hereinafter), enables an optimal dispense of the products, by offering a slope with an angle advantageously selected to enable the descent of the products as the products are taken, by the users, in the distribution compartment, without blocking or clogging.

According to a particular embodiment, the dispenser also comprises at least one movable upper cap having at least a closed position and an open position for the introduction of said at least one product refill, and the side faces are substantially vertical and perpendicular to said rear face and extend from said cap up to the external end of said distribution compartment.

Thus, the side walls of the dispenser have a particular shape conferring thereon a first technical effect of reinforcing the rigidity of the dispenser, by securing the storage and distribution compartments together. Indeed, because of its location and its shape, the distribution compartment forms a point of weakness at its connection with the storage compartment(s), this weakness being reduced and even eliminated thanks to the reinforcement of the side walls of the dispenser.

In addition, this specific shape provided for the side walls also allows the dispenser not to have any acute angles at the distribution compartment which forms an excrescence in the lower portion of the dispenser. Thus, regardless of the shape of the distribution compartment, the side walls have a shape adapted to extend so as to encompass the distribution compartment on each side.

For example, the distribution compartment has a shape:
in a circle arc, or
in V, or
flat-bottomed with a flange, perpendicular to the bottom or inclined with respect to the bottom.

Thus, the shape of the distribution compartment may depend, for example, on manufacturing and material constraints. For example, a circle arc shape (or half-gutter) might be difficult to achieve in certain materials or according to some manufacturing processes: for example when the other portions of the dispenser could be made by bending a material such as thin sheet metal, obtaining a rounded shape is not possible by bending, while a flat-bottomed shape with a flange could be more easily achievable.

Regardless of the shape of the distribution compartment, the latter should be able to allow access to a product of each of the types of products provided in the dispenser, as well as the proper holding of the products while waiting for them to be used. Thus, the gutter-like shape should be deep enough and the flange of a flat-bottomed compartment should be high enough to retain products of each type.

In addition, according to a particular aspect, the distribution compartment has at least one partition wall opposite said at least one wall of said storage compartment.

According to this embodiment, a partition wall is provided at the distribution compartment, so as to contain a product type when it descends from the refill. In particular, this wall is useful for small-sized products, such as tampons without applicators, which might move in the distribution compartment and mix with other products.

In addition, as described hereinafter, the refills containing these small products do not have, unlike those for larger products, product retention notches. Hence, tampons without an applicator are more likely than others to move during their descent in the distribution compartment and should therefore be kept in a dedicated space, thanks to this wall.

The present technique also relates to a product refill comprising a plurality of menstrual products intended to be inserted into a menstrual product dispenser as described before in connection with the embodiments. Such a refill comprises a substantially parallelepiped upper portion with a front face with a length larger than a rear face and a base having an angle larger than 90° with said rear face, and the front face is pre-cut according to a predetermined shape in the lower portion for opening thereof and distributing the products it contains.

Hence, the menstrual product dispenser is intended to receive one or several product refill(s), with a substantially parallelepiped shape with a "bevelled" base, which are inserted solid and closed in the dispenser. Hence, they have a pre-cut enabling opening thereof, in their lower part, once inserted into the dispenser by the person in charge of supply.

In addition, the "bevelled" shape of the base of the refills is advantageously intended to facilitate the descent of the products in the refill, as the products are taken, by users, in the distribution compartment of the dispenser.

For example, such a refill is made of cardboard material or of rigid paper.

According to a particular feature, the predetermined pre-cut shape comprises at least one notch intended to be located opposite a similar notch provided in said menstrual product dispenser when said refill is inserted into said menstrual product dispenser.

Hence, the opening of the refill is facilitated by the presence of a notch in the pre-cut, coinciding with a similar notch in the front face of the dispenser, more specifically of the refill storage compartment. In this manner, the person in charge of supplying the dispenser presses on the lower portion of the refill accessible through the lower opening provided in the front face of the dispenser, at the notch, so as to be able to use the notch of the refill like a tab to complete cutting of the lower portion of the refill and the complete opening of the base thereof.

In addition, as already indicated hereinabove in connection with the dispenser, this notch, once the refill is opened, facilitates a user taking the product in the distribution compartment. Indeed, for hygienic reasons, the opening intended to make the products accessible being restricted, so as to make only one product per product type accessible, it might be difficult to take the product without this notch.

Preferably, the notch is centred with respect to the width of the refill.

Like for the notches provided in the storage compartment, and as described before, the size of this notch of the refill, and more particularly its height, could be variable. According to a first variant, it has a height of about one centimetre. According to a second variant, it has a height of up to ten centimetres, so as to further allow a possible release of the products in the refill, while allowing visibility of the stock of products remaining in the refill.

According to a particular aspect, the predetermined pre-cut shape comprises at least one tab forming an excrescence.

Thus, once the refill is opened, it has a central notch enabling gripping of the product in the distribution compartment, and at least one tab allowing holding the products in the refill, in order to limit to one product, per type, accessible in this distribution compartment.

Advantageously, and particularly for large-sized products such as tampons with an applicator or sanitary napkins, two tabs are provided on the front face of the refill, on either side of the central notch, so as to ensure a proper holding of the products in the refill once opened.

It should be noted that the refills containing small products (such as tampons without an applicator) do not have these tabs, the adjusted size of the refill and of the corresponding storage compartment as well as the presence of a wall in the distribution compartment allowing limiting the number of accessible products.

In addition, the pre-cut also extends over the two side edges and the lower edge of the refills so as to enable complete removal of the pre-cut material and thus allow access to the products that descend and leave the refill.

PRESENTATION OF THE FIGURES

Other aims, features and advantages of the proposed technique will appear more clearly upon reading the following description, given as a simple illustrative, and non-limiting, example in connection with the figures, among which:

DETAILED DESCRIPTION OF EMBODIMENTS OF THE INVENTION

Figure 1:
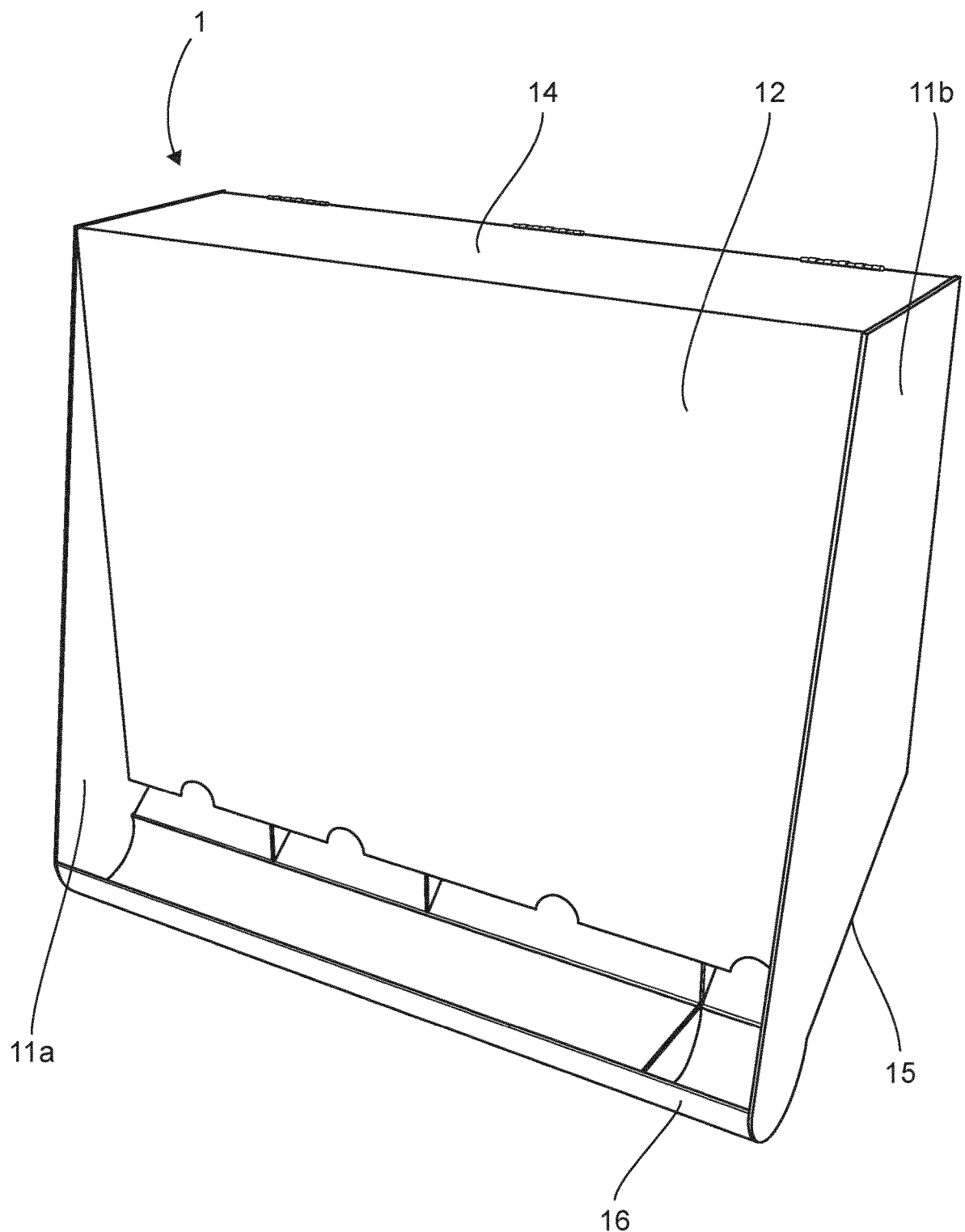
FIG. 1 shows a menstrual product dispenser, without any refill, according to an embodiment of the proposed technique.

The general principle of the proposed technique is based on a menstrual product dispenser comprising at least one compartment for storing menstrual products, of several types, contained in refills and a product distribution compartment arranged so that only one product of each type is accessible to the users.

Thus, the supplying of the dispenser with products according to the proposed solution is facilitated thanks to the use of closed refills to be inserted into the dispenser, and the hygiene rules related to the types of dispensed products are met, at the time of supply of the dispenser thanks to the closed refills and at the time of access to the products thanks to the limitation to a single product accessible at a time.

As illustrated in FIG. 1 to 5, a dispenser 1 according to an embodiment of the proposed technique therefore comprises a rear face for attaching thereof to a support, most commonly a wall in a toilet for example. Such a dispenser 1 also comprises two side faces 11a and 11b, and a front face 12.

In addition, the dispenser 1 comprises at least one product storage compartment (13a, 13b, 13c, 13d), adapted to receive a product refill as described in more detail hereinafter. To enable this insertion of refill(s) into the dispenser 1, a movable upper cap 14 is therefore provided which could be opened to supply the dispenser 1 and could be closed to prevent access to the refills and therefore to the products.

According to several variants, the cap 14 could be locked, or simply designed so that the side faces 11a and 11b cover the field of the cap 14, thus preventing access thereto. This provides a locking form that is easy to operate, and the persons in charge of supplying the dispenser will have a magnet allowing opening the cap to insert the refills. Of course, other locking forms could be implemented, as needed.

The dispenser 1 also comprises a base 15, secured to the rear face 10 and the side faces 11a and 11b, for the lower holding of the refills in the dispenser.

According to a particular feature, the base 15 is not perpendicular to the rear face (the dispenser therefore does not have a parallelepiped shape) but it forms an angle larger than 90° with the rear face, so as to have a slope identical to that formed by the base of the refills (cf. the description hereinafter) in order to facilitate the flow of products towards the dispensing area.

Figure 4B:
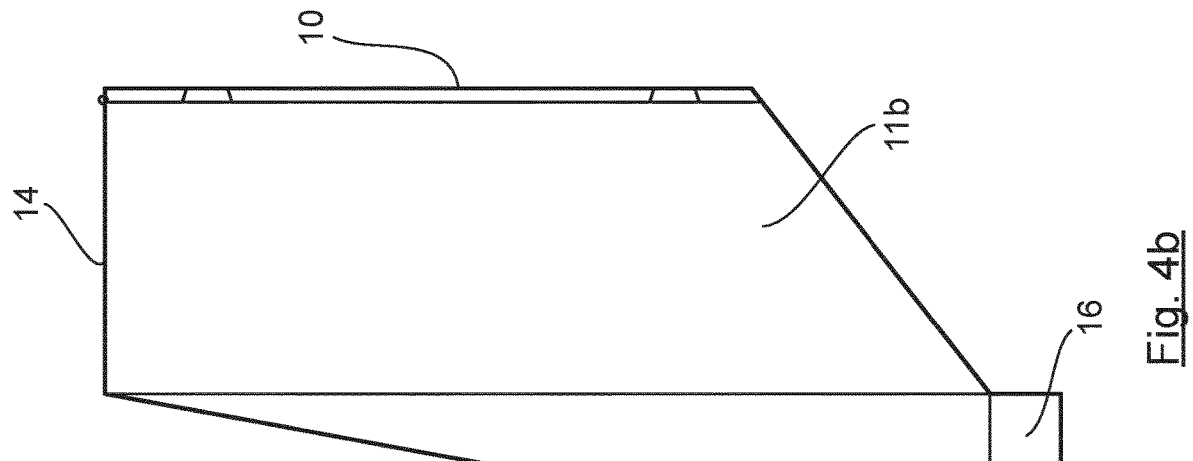
FIG. 4b shows a side view of the menstrual product dispenser of FIG. 1, according to a second variant of the distribution compartment.
Figure 4A:
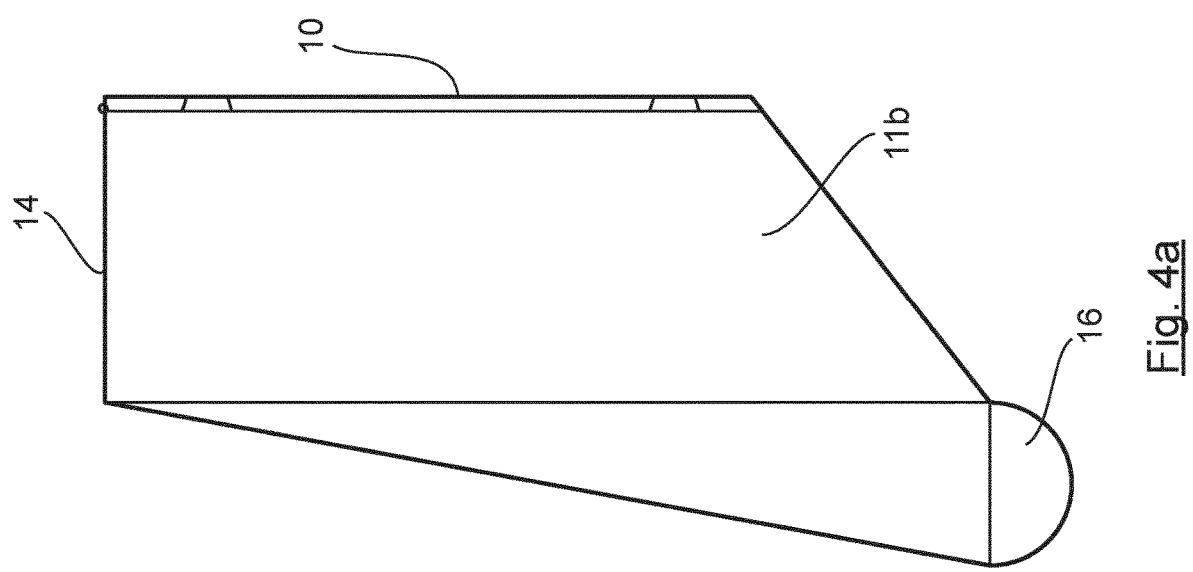
FIG. 4a shows a side view of the menstrual product dispenser of FIG. 1, according to a first variant of the distribution compartment.

This dispensing area corresponds to a distribution compartment 16, secured, along its length, to the base 15 of the dispenser. This distribution compartment may be in several forms, such as a circle arc shape (half-gutter) as illustrated in FIG. 4a, in V, or still a flat bottom with a flange to retain the products, as illustrated in FIG. 4b. As already indicated, the shape of the distribution compartment may be selected according to technical constraints of manufacture, of material, or still of aesthetic wishes, as long as it meets the technical constraints related to the dispenser itself which require that only one product, per type of product, is accessible in the distribution compartment 16.

In addition, this distribution compartment 16 should not be too deep to allow for an easy gripping of the products by the users, while ensuring good holding of the products which should not fall from the dispenser otherwise they will be unusable, still for hygienic reasons.

One of the particularities of the dispenser 1 also concerns the opening 121 formed in the front face 12 to allow accessibility to one product per product type, when the product descends from the refill to be positioned in the distribution compartment 16. Indeed, this opening 121 formed in the front face has a shape and dimensions advantageously determined so as to obtain this technical effect of "releasing" a single product descending from a refill while making it accessible, i.e. by enabling it to reach the distribution compartment 16. The opening 121 should also enable the users to take the product in the distribution compartment 16.

Finally, an additional difficulty in determining this opening 121 concerns the multiplicity of the types of products that could be dispensed, and in particular the multiplicity of their shapes and sizes. Thus, tampons, with or without applicators, with different sizes are dispensed alongside sanitary napkins, also with different sizes.

Finally, as described hereinafter, this opening 121 are also intended to enable opening of the refills inserted in the storage compartments 13a to 13d, and should enable the person in charge of the dispenser supply, to access the base of the refill in order to cut it, according to the provided pre-cut.

For this purpose, the opening 121 is not rectilinear but has at least one so-called gripping notch 122, advantageously provided for each storage compartment of the dispenser and preferably centred with respect to the width of each compartment. This notch 122 also enables the person who inserts the refills to access the base of the refill in order to open them, as described hereinafter. The shape (for example a circle arc like one) and the dimensions of these gripping notches (122a to 122d) are therefore advantageously defined to allow obtaining these various technical effects: opening of the refills and assisting in gripping a product in the distribution compartment.

Figure 2A:
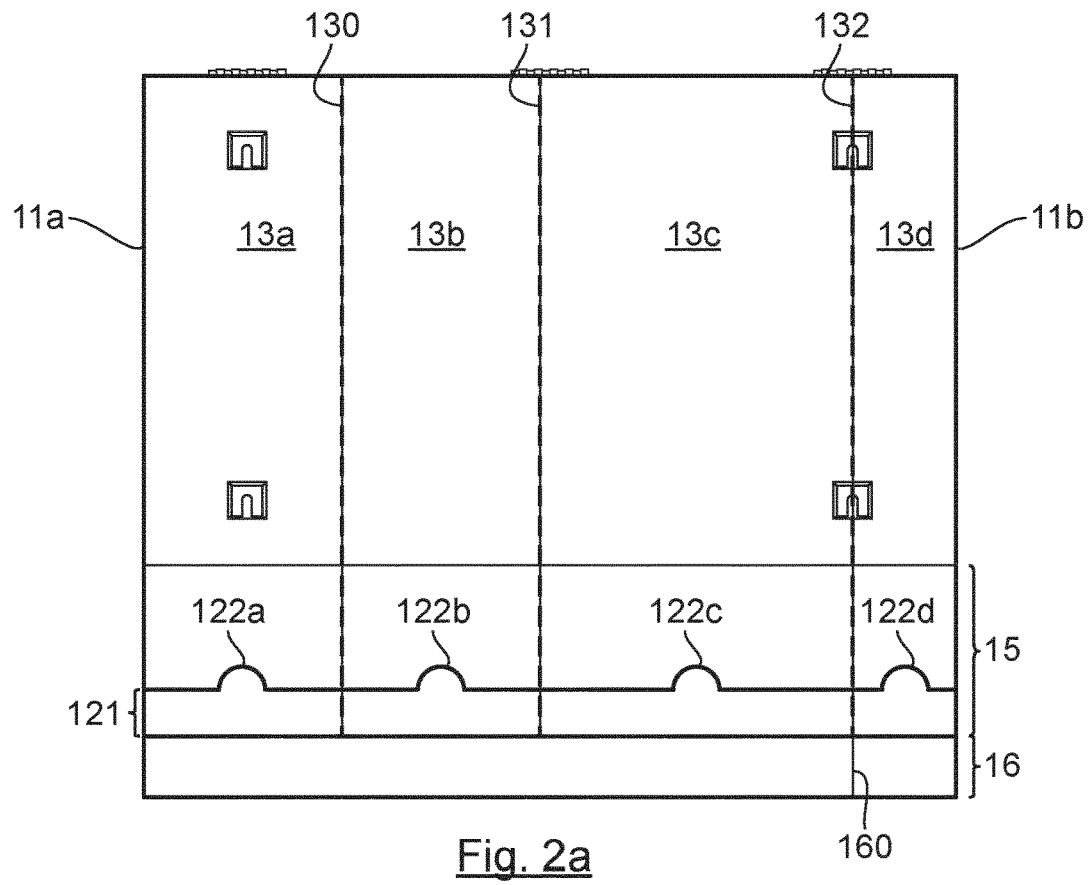
FIG. 2a shows a front view of the menstrual product dispenser of FIG. 1, according to a first variant.

For example, according to a first variant illustrated in FIG. 2a, the notches 122a to 122d have substantially identical dimensions, and in particular a height of about 1 centimetre.

Figure 2B:
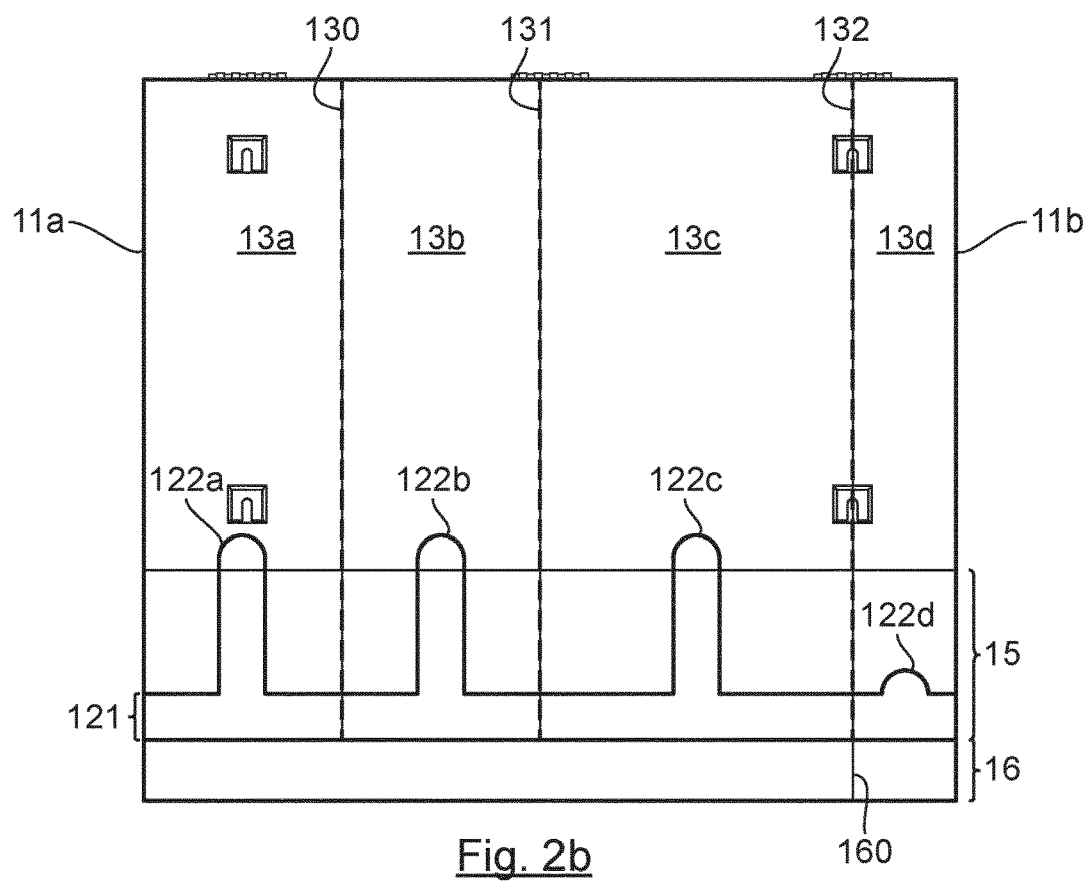
FIG. 2b shows a front view of the menstrual product dispenser of FIG. 1, according to a second variant.

According to a second variant illustrated in FIG. 2b, the notches 122a to 122c have substantially identical dimensions, and in particular a height that could range up to ten centimetres, so as to enable a possible release of the products in the refill, while allowing visibility on the stock of products remaining in the refill. Hence, these notches 122a to 122c rather correspond to vertical slots. However, the notch 122d has a smaller size, and in particular a height of about 1 centimetre, in order to prevent a possible come-out of the (small-sized) products out of the refill.

As detailed hereinafter with examples of possible dimensions for making such a dispenser, the opening 121 should be defined very accurately to comply with all these constraints and allow obtaining the desired technical effects.

As already indicated before, the dispenser 1 is advantageously intended to offer several types of different menstrual products, thanks to several storage compartments 13a . . . 13i. According to the illustrated examples, four compartments are provided, receiving four refills containing four different types of products. Of course, it is possible to provide more or less storage compartments, as needed, the characteristics of the dispenser remaining the same as soon as there are at least two compartments.

Indeed, as soon as the dispenser 1 includes at least two storage compartments, provision is made for these compartments to be separated by a vertical wall 130 . . . 13i, substantially parallel to the side faces of the dispenser 1. According to the illustrated examples, the four storage compartments 13 to 13d are respectively separated by walls 130, 131 and 132. These walls 130, 131 and 132 allow not only guiding the refills during their insertion, but also stabilising them in their respective storage compartment, once inserted, even in the absence of a refill in the neighbouring storage compartment.

Figure 3:
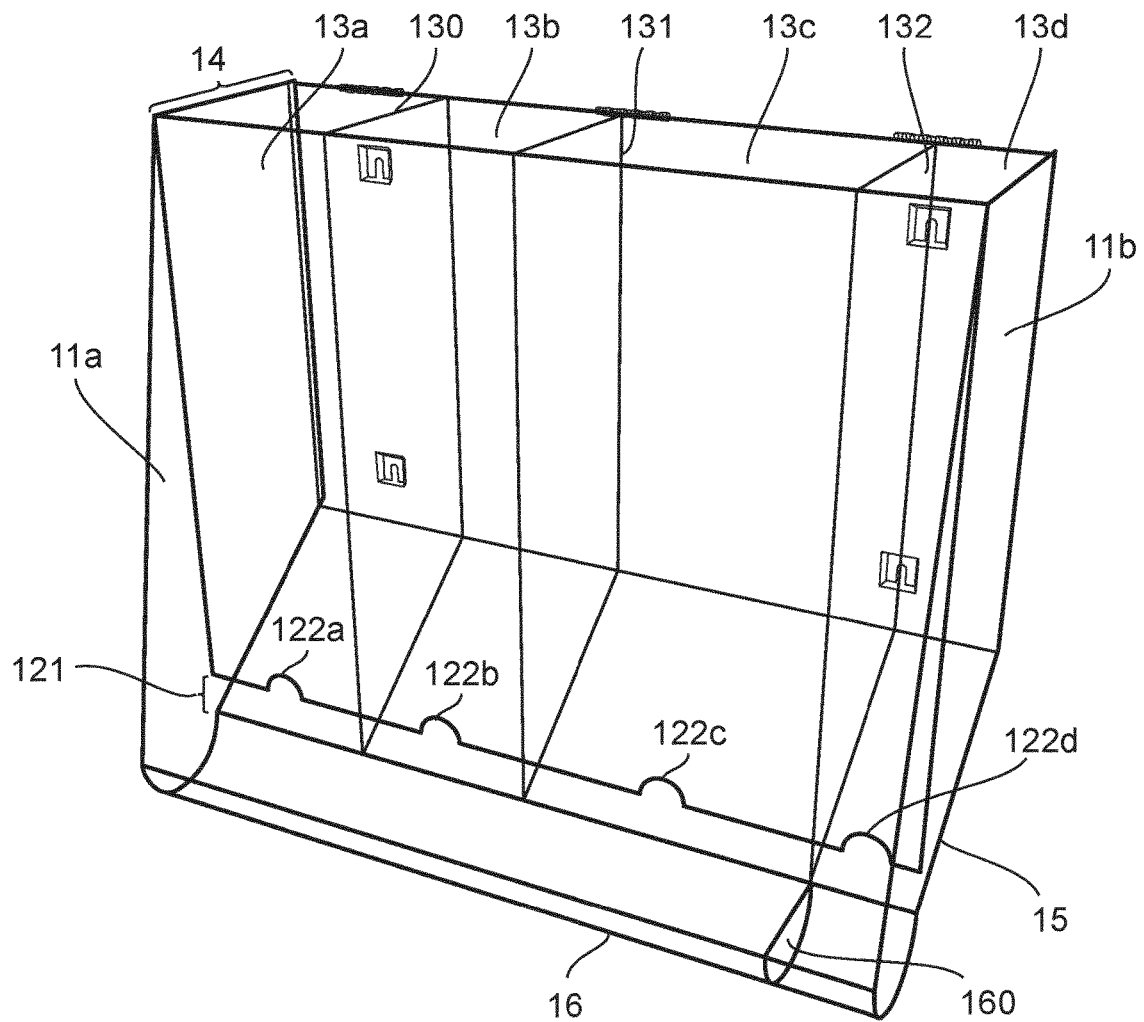
FIG. 3 shows a perspective view of the menstrual product dispenser of FIG. 1, according to the first variant.
Figure 5:
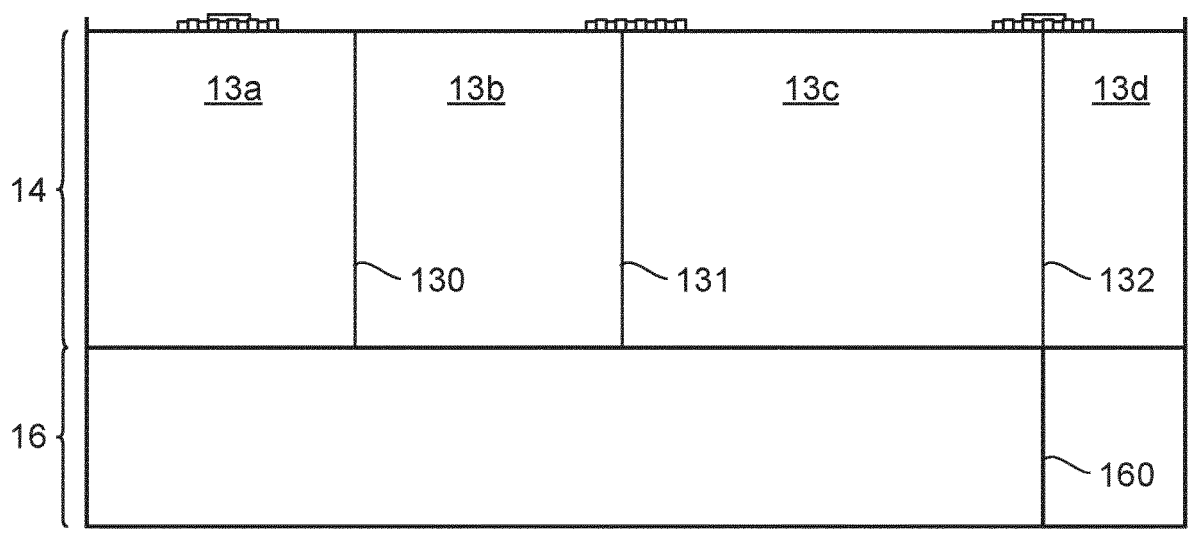
FIG. 5 shows a top view of the menstrual product dispenser of FIG. 1.

According to a first second variant, illustrated for example in FIG. 3 and in FIG. 5, a wall is formed by a partition extending from the rear face to the front face of the dispenser, over all or portion of the height of the storage compartment.

According to a second variant, not illustrated, a wall is formed by a simple rail, more or less wide, over all or portion of the height of the storage compartment, secured to the rear face or the front face of the dispenser.

Any other embodiment of such walls could be considered as long as they allow obtaining the desired technical effect, namely the guidance and holding of the refills in their dedicated storage compartment.

Another aspect of the dispenser 1 will now be described, in connection with FIGS. 3 and 4a and 4b in particular, relating to the shape of the side faces 11a and 11b. Indeed, according to an embodiment of the proposed technique, the side faces 11a and 11b, substantially vertical and perpendicular to the rear face, extend beyond the front face 12 in their lower portions so as to encompass the distribution compartment 16. This feature allows, on the one hand, reinforcing the rigidity of the dispenser, by greatly reducing, or even eliminating, the point of weakness that the distribution compartment 16 might form (due to its shape and its unique area of securing to the rest of the dispenser) and, on the other hand, avoiding any sharp angle outside the dispenser. Finally, this extension of the side walls also allows providing flanges on each side of the distribution compartment 16, in one piece and therefore easy to manufacture and solid.

Finally, the distribution compartment 16 has, according to a particular implementation, at least one partition wall 160, opposite a separation between two storage compartments, for example, as illustrated in FIGS. 2*a*, 2*b*, 3 and 5, opposite the wall 132 separating the storage compartments 13*c* and 13*d*. In particular, this separation wall 160 enables the product descending from the refill inserted into this storage compartment 13*d* to be held in the distribution compartment 16, without moving and therefore without being mixed for example with the product descending from the refill inserted into the storage compartment 13*c*. Advantageously, this wall is useful when the products are small-sized, such as tampons without an applicator.

Before describing in more detail another aspect of the present solution, relating to the menstrual product refills intended to be inserted into a dispenser as described hereinabove, the dimensions of a dispenser according to an embodiment of the present invention are presented hereinafter, suited for the dispense of four types of menstrual products, via four storage compartments:

430 millimetres in total width,
351.5 millimetres in total height, up to the external end of the base 15 (without the depth of the distribution compartment 16),
104.25 millimetres in width of the storage compartment 13*a*,
103.5 millimetres in width of the storage compartment 13*b*,
163.5 millimetres in width of the storage compartment 13*c*,
54.25 millimetres in width of the storage compartment 13*d*,
25 millimetres in width of each gripping notch 122,
25 millimetres of opening 121 of the front face 12,
115 millimetres in depth of the storage compartments 13*a* to 13*d*,
188 millimetres of maximum depth, including the depth of the storage compartments 13*a* to 13*d* and the width of the distribution compartment 16,
259 millimetres in height of the rear face 10,
68 millimetres in width of the distribution compartment 16,
34 millimetres in depth of the distribution compartment 16.

Figure 6B:
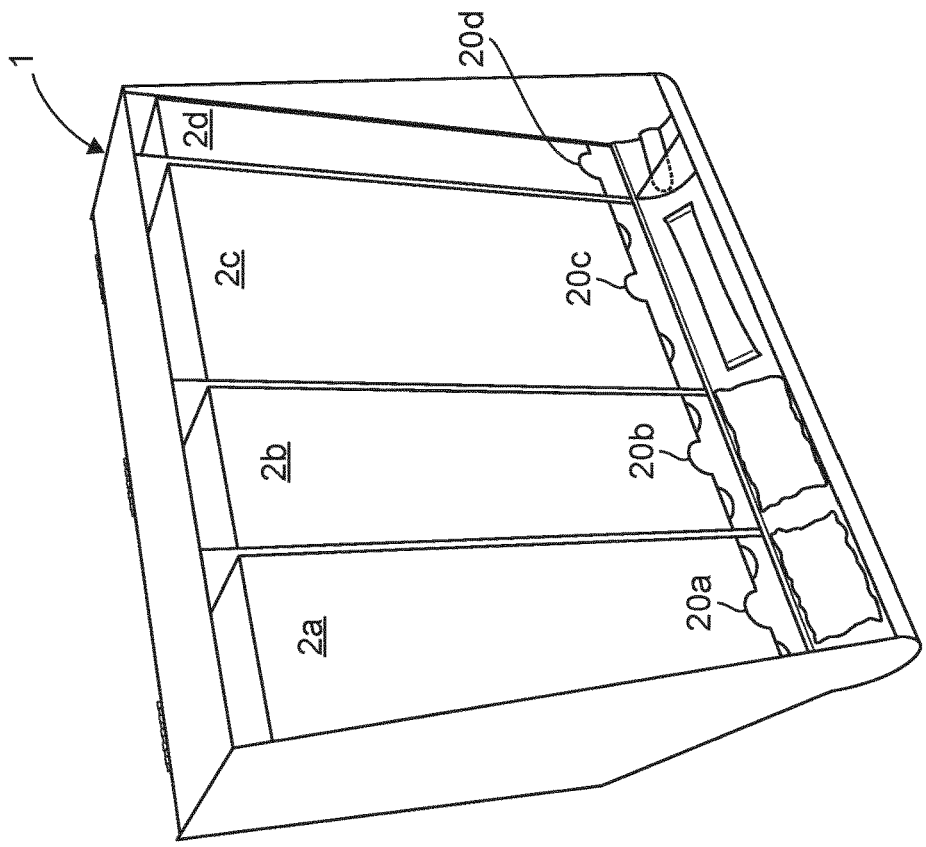
FIG. 6b shows a menstrual product dispenser with open refills, according to the first variant of an embodiment of the proposed technique.
Figure 6A:
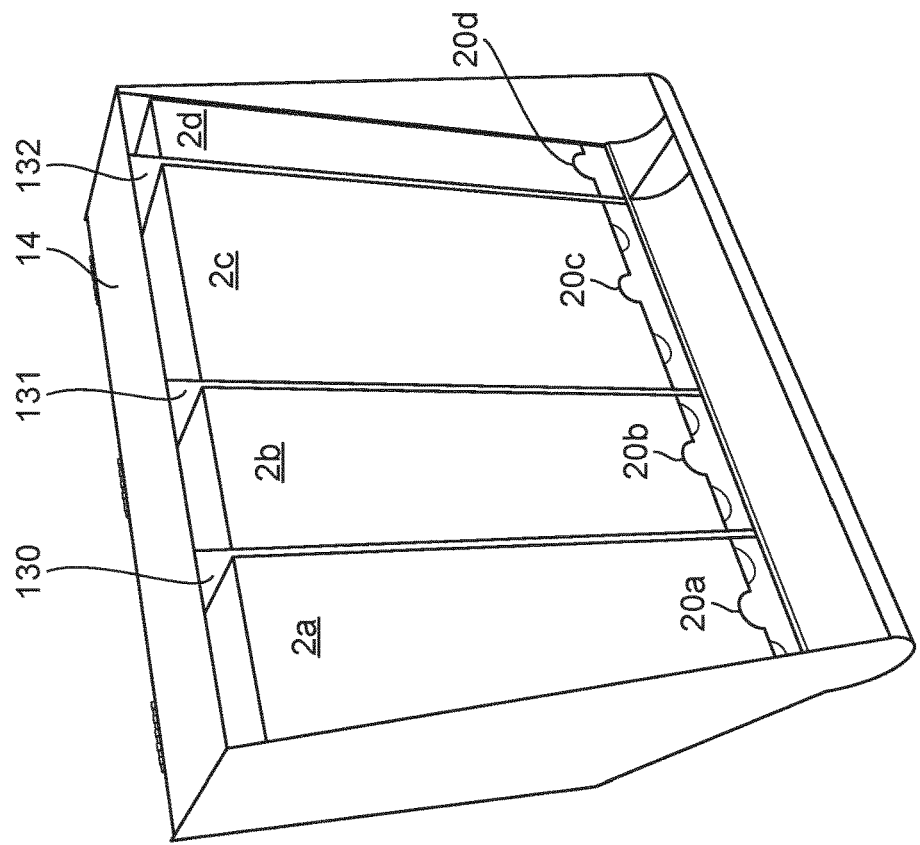
FIG. 6a shows a menstrual product dispenser with closed refills, according to a first variant of an embodiment of the proposed technique.

FIGS. 6*a* and 6*b* now illustrate a dispenser 1 according to a first variant of an embodiment described hereinabove and in which four product refills 2*a* to 2*d* are inserted, respectively in four storage compartments 13*a* to 13*d*, respectively separated by walls 130, 131 and 132, in this example.

In FIG. 6*a*, the refills 2*a* to 2*d* are closed, as they are inserted by the person in charge of supplying the dispenser 1, while in FIG. 6*b*, the refills 2*a* to 2*d* are open, the white area between the lower portion of the front face and the distribution compartment 16 corresponding to the interior of the refills, the products also being illustrated in the distribution compartment 16.

Figure 7C:
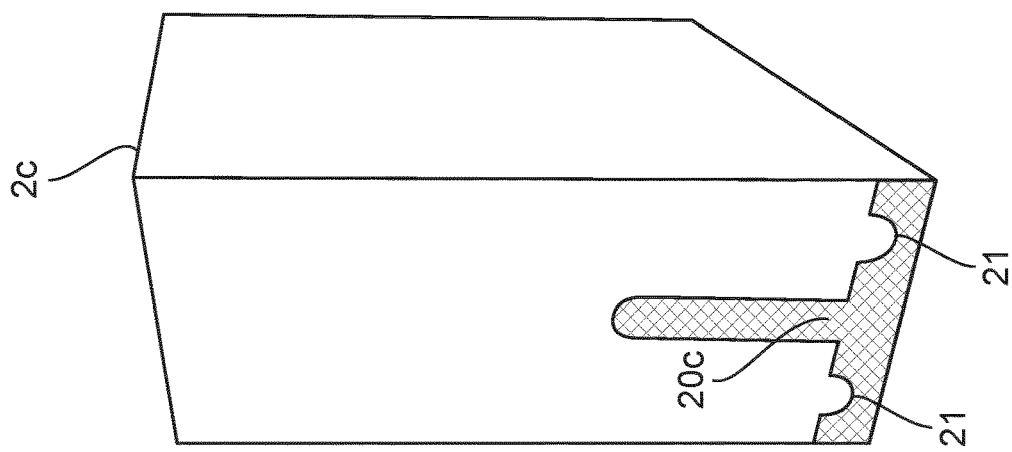
FIG. 7c shows an example of a refill for a dispenser of large-sized menstrual products, according to a second variant of an embodiment of the proposed technique.
Figure 7B:
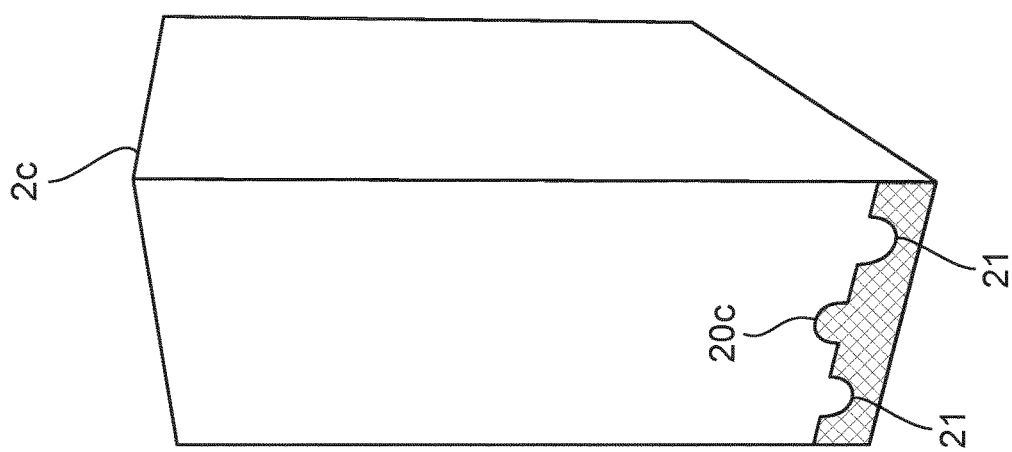
FIG. 7b shows an example of a refill for a dispenser of large-sized menstrual products, according to a first variant of an embodiment of the proposed technique.
Figure 7A:
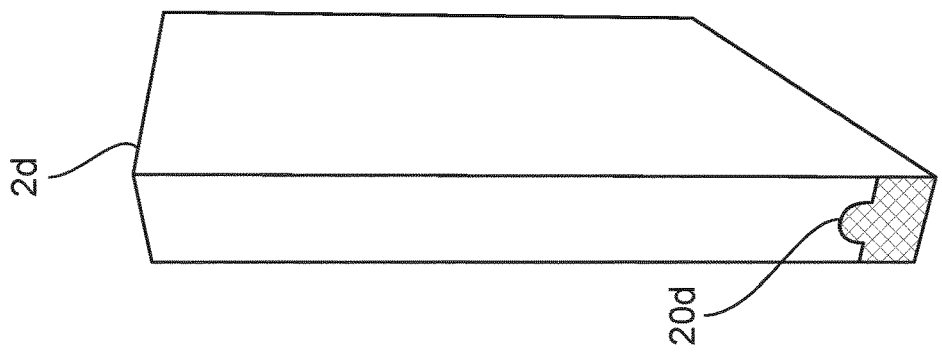
FIG. 7a shows an example of a refill for a dispenser of small-sized menstrual products, according to an embodiment of the proposed technique.

Two examples of product refills are illustrated in FIGS. 7*a*, 7*b* and 7*c*, for two types of products such as tampons without an applicator, narrow refill illustrated in FIG. 7*a* and intended to be inserted into the storage compartment 13*d*, and tampons without an applicator, larger refill illustrated in FIGS. 7*b* and 7*c*, according to two variants, and intended to be inserted into the storage compartment 13*c*.

As is the case for the base of the dispenser, a menstrual product refill according to an embodiment of the proposed technique comprises a substantially parallelepiped upper portion, yet with a front face with a larger length than a rear face and a base having an angle larger than 90° with the rear face, so that the storage compartments of the dispenser conform with the shape of each refill. Indeed, this inclined base allows controlling the descent of the products in the refill, as their used, while avoiding any blockage or clogging and limiting to a single product accessible in the distribution compartment.

For example, the angle formed between the base and the rear face (for a refill or for the dispenser) is advantageously around 130 degrees.

In addition, the front face of each refill is pre-cut according to a predetermined shape in the lower portion to enable on the one hand opening thereof during its installation in the dispenser and also distributing the products it contains, as they are used.

Indeed, in order to facilitate the supply of the dispenser and to avoid any direct handling of the menstrual products, each refill is inserted closed and the pre-cut allows facilitating opening thereof.

Thus, the pre-cut comprises in particular a notch (20*a* to 20*d* according to this embodiment), located centred with respect to the width of the refill and intended to be located opposite the notch 122*a* . . . 122*d* provided on the front face of the dispenser, as described before. It is on this notch 20*a* to 20*d* that the person in charge of supplying the dispenser presses, via the notch 122*a* . . . 122*d* provided on the front face of the dispenser, to initiate cutting of the lower portion of the refill, for total opening thereof. Once this notch 20*a* to 20*d* has been cut, it could serve as a tab to pull on the lower portion of the refill and thus cut on either side of the notch, including the side edges and the lower edge, in order to completely detach the lower portion of the front face of the refill.

According to a first variant illustrated in FIG. 6*a* and FIG. 6*b*, the notches 20*a* to 20*d* have substantially identical dimensions, and in particular a height of about 1 centimetre, in order to coincide with the corresponding notches provided on the refills.

Figure 6C:
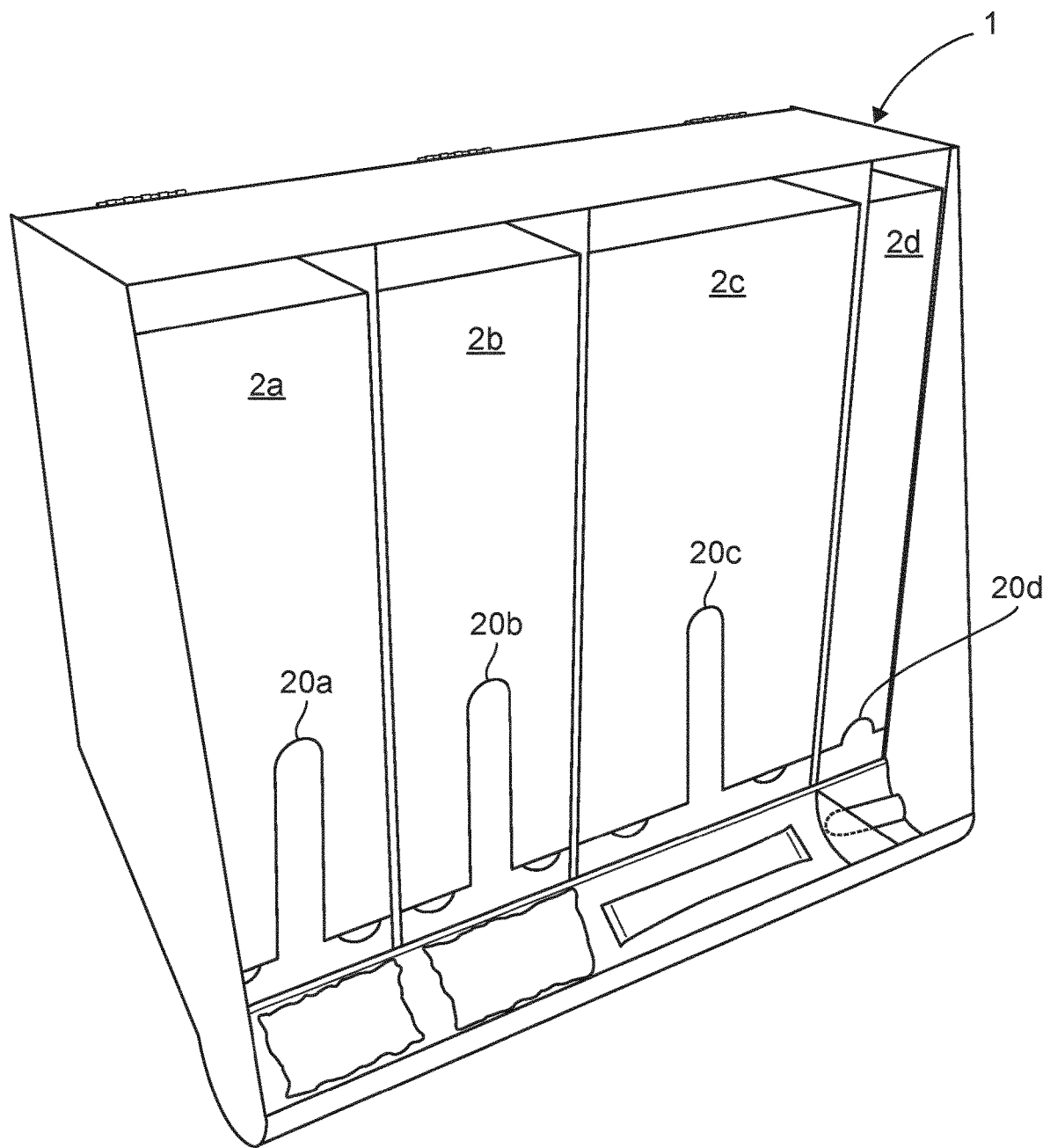
FIG. 6c shows a menstrual product dispenser with open refills, according to a second variant of an embodiment of the proposed technique.

According to a second variant illustrated in FIG. 6*c*, the notches 20*a* to 20*c* have substantially identical dimensions, and in particular a height that could be up to ten centimetres, so as to enable a possible release of the products in the refill, while allowing visibility on the stock of products remaining in the refill. Hence, these notches 20*a* to 20*c* rather correspond to vertical slots. However, the notch 20*d* has a smaller size, and in particular a height of about 1 centimetre, in order to prevent a possible come-out of the (small-sized) products out of the refill.

The obtained result, i.e. refills opened once inserted into the dispenser, is illustrated for example in FIG. 6*b*.

Moreover, in order to optimise the desired technical effect consisting in having access to only one product of each type in the distribution compartment 16 of the dispenser, the pre-cut shape of the lower portion of each refill also comprises at least one tab 21 forming an excrescence of the refill when it is open, as illustrated in FIG. 7*b*. Indeed, this tab 21 is intended to retain the products in the refill, with the exception of the product intended to be accessible in the distribution compartment. For example, and as illustrated in FIG. 7*b*, a refill comprises two tabs 21, located on either side of the notch 20, in particular for the refills containing large-sized products, such as tampons with applicators or towels. Thus, in the example illustrated in FIGS. 6*a*, 6*b* and 7*a*, the refills 2*a*, 2*b* and 2*c* have two tabs 21 and a notch 20A, 20*b* and 20*c*, while the refill 2*d* has only one notch 20*d* because of the small size of the products it contains.

Thus, the size of the opening provided in the front face of the dispenser and these tabs provided in the lower portion of the refills allow obtaining the desired technical effect.

Moreover, in FIG. 7a to 7c, the "cuttable" portion of the refill is hatched. Thus, it is in possible particular to clearly visualise the notches 20d and 20c, and in particular the two variants of the notch 20c, respectively with a substantially identical size (height of about 1 centimetre) to the notch 20d as illustrated in FIG. 7b, and with a larger size (in particular a height of up to ten centimetres) as illustrated in FIG. 7c. As already described, this larger size of the notch, which is similar to a vertical slot, enables a possible release of the products in the refill, while allowing visibility of the stock of products remaining in the refill.

Hence, thanks to a menstrual product dispenser and refills containing the products intended to be inserted therein, the present technique allows providing a solution for the dispense of menstrual products of several types, while complying with the hygienic constraints associated with these products, ergonomically both for the users and for the persons in charge of supplying the dispensers.

The invention claimed is:

1. A menstrual product dispenser comprising:
   a rear face for attaching said dispenser to a vertical support, first and second side faces and a front face;
   at least one storage compartment suitable for receiving at least one closed product refill comprising a plurality of menstrual products of a same type,
      said at least one product refill having a substantially parallelepiped upper portion with a front face with a length larger than a rear face and a base having an angle larger than 90° with said rear face;
      said at least one storage compartment being shaped to conform with the shape of said at least one product refill; and
   at least one distribution compartment for distributing at least one of said menstrual products,
   wherein the front face of the dispenser has at least one lower opening opposite said at least one distribution compartment, said at least one lower opening having a shape and dimensions suited for distributing a single menstrual product per type in said distribution compartment, and
   wherein said at least one lower opening has at least one gripping notch designed to be located opposite at least one notch of a predetermined shape which is pre-cut in the front face of said at least one product refill, in its lower portion, for opening thereof and distributing the products that the at least one product refill contains when said at least one product refill is inserted into said menstrual product dispenser.

2. The menstrual product dispenser according to claim 1, wherein the dispenser comprises at least two storage compartments separated by a vertical wall substantially parallel to said first and second side faces, said at least two storage compartments each configured to receive a product refill.

3. The menstrual product dispenser according to claim 1, wherein the dispenser also comprises a base having an angle larger than 90° with said rear face.

4. The menstrual product dispenser according to claim 1, wherein the dispenser comprises at least one movable upper cap having at least a closed position and an open position for introduction of said at least one product refill, and wherein said first and second side faces are substantially vertical and perpendicular to said rear face and extend from said cap up to an external end of said distribution compartment.

5. A product refill comprising:
   a closed container containing a plurality of menstrual products to be inserted into a menstrual product dispenser;
   a substantially parallelepiped upper portion with a front face with a length larger than a rear face and a base having an angle larger than 90° with said rear face,
   wherein said front face is pre-cut according to a predetermined shape in a lower portion for opening thereof and distributing the products that the product refill contains.

6. The product refill according to claim 5, wherein said predetermined pre-cut shape comprises at least one notch to be located opposite a similar notch provided in a menstrual product dispenser when said product refill is inserted into said menstrual product dispenser.

7. The product refill according to claim 5, wherein said predetermined pre-cut shape comprises at least one tab forming an excrescence.

8. The menstrual product dispenser according to claim 1, wherein the dispenser further comprises the at least one closed product refill contained in the at least one storage compartment.

* * * * *